United States Patent [19]

Meilland

[11] Patent Number: Plant 7,624

[45] Date of Patent: Aug. 20, 1991

[54] ROSE PLANT—MEIDIAPLOU VARIETY

[75] Inventor: Alain A. Meilland, Antibes, France

[73] Assignee: The Conard-Pyle Company, West Grove, Pa.

[21] Appl. No.: 482,719

[22] Filed: Feb. 21, 1990

[51] Int. Cl.[5] ..... A01H 5/00

[52] U.S. Cl. ..... Plt./20

[58] Field of Search ..... Plt./28, 29, 20, 21

[56] References Cited

U.S. PATENT DOCUMENTS

P.P. 3,779 9/1975 Warriner ..... Plt. 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms attractive double blossoms which are strawberry red on the upper surface and cardinal red on the lower surface. Such blossoms have very firm petals and are long lasting either on the plant or when cut and placed in a vase. The plant exhibits an upright growth habit, very vigorous vegetation, and is well suited for greenhouse forcing for cut flower production. Additionally, the plant exhibits very good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Meinastur variety (U.S. Plant Pat. No. 3,926) with the Reine Des Roses variety (non-patented in the United States). The Meinastur variety sometimes is known as the ALPHA variety, and Reine Des Roses variety sometimes is known as the Königin Der Rosen variety. The male parent (i.e., the pollen parent) was the MEIRODIUM variety (U.S. Plant Pat. No. 4,037). The parentage of the new variety can be summarized as follows:

(Meinastur × Reine Des Roses) × Meirodium.

The seeds resulting from the above pollination were sown and 74 small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long lasting double blossoms having very firm petals which are strawberry red on the upper surface and cardinal red on the under surface,
(b) exhibits an upright growth habit,
(c) exhibits very vigorous vegetation,
(d) is particularly suited for cut flower production in a greenhouse, and
(e) exhibits excellent disease resistance.

The blossoms are long lasting either on the plant or when cut and placed in a vase.

The new variety well meets the needs of the horticultural industry for all uses and is particularly well suited for cut flower production.

The new variety has been found to undergo asexual propagation by a number of routes, including budding, grafting, cuttage, etc. The characteristics of the new variety have been found to be strictly transmissible on a stable basis by such asexual propagation from one generation to another.

The new variety has been named the Meidiaplou variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indicia* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
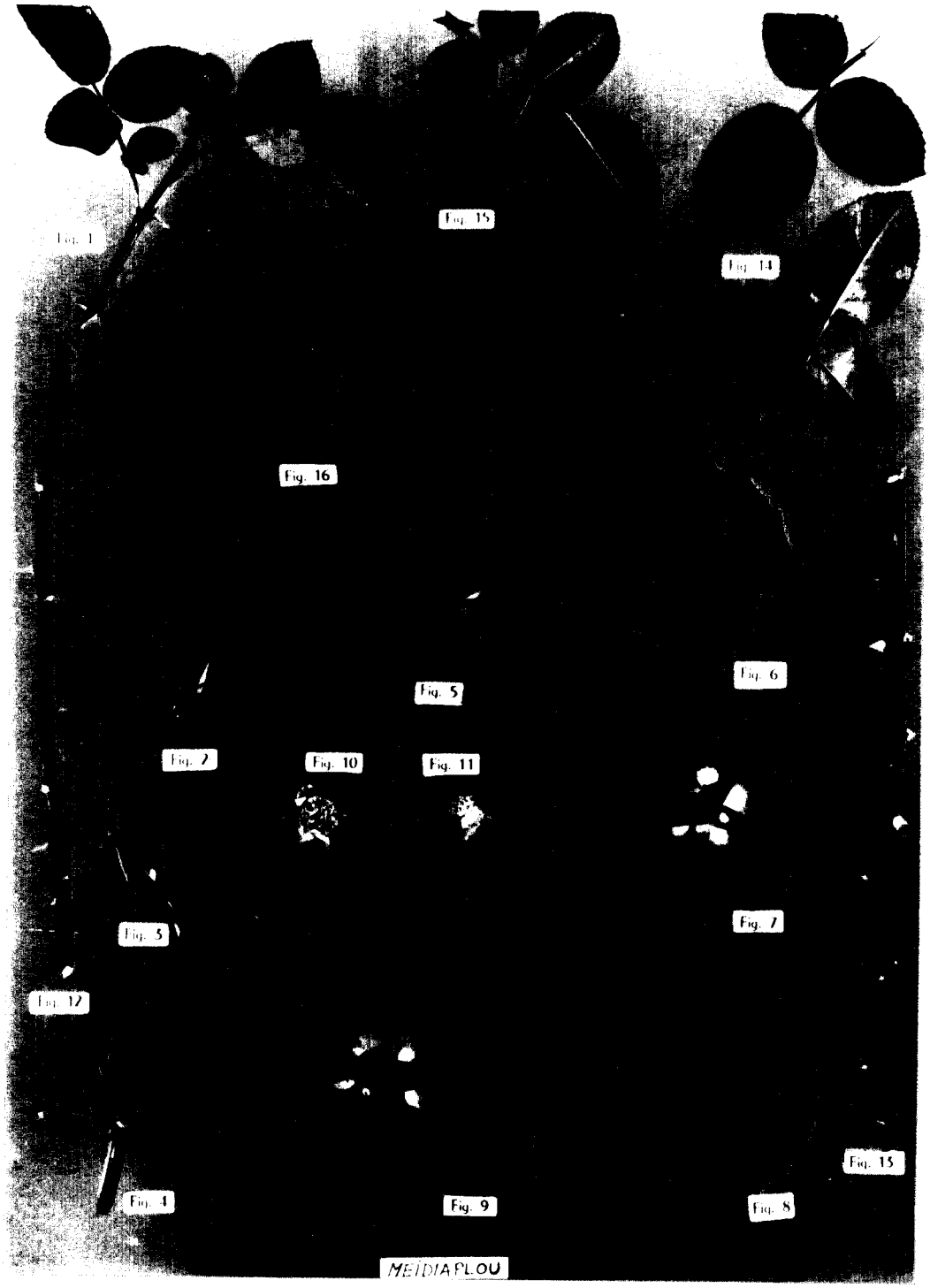
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of a pair of leaves having three leaflets with the upper surface being shown on the top and the under surface being shown on the bottom.
FIG. 15 illustrates specimens of a pair of leaves having five leaflets with the under surface being shown on the top and the upper surface being shown on the bottom.
FIG. 16 illustrates a specimen of a leaf with seven leaflets—plan view—under surface.

The chart used in the identification of the colors is that of The Royal Horticultural Society (R.H.S. Colour Chart). The description is based on the observation of two year old plants made during November while budded on *Rosa indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 50 to 70 cm.

*Habit.*—Upright.

Branches:

*Color.*—Young stems: bronze green, Yellow-Green Group 146A, more or less stained with reddish coloration. Adult wood: medium green, Yellow-Green Group 146B.

*Thorns.*—Size: medium. Quantity: numerous. Color: pinkish on young stems and greenish changing to tan mature wood.

Leaves:

*Stipules.*—Adnate, pectinate, very wide and linear.

*Petioles.*—Upper surface: striped reddish brown on young foliage and medium green on adult foliage with more or less glandular edges. Under surface: light green and smooth.

*Leaflets.*—Number: 3, 5 (most often), and 7. Shape: oval. Serration: single and regular. Texture: very consistent. General appearance: dense, semi-dull, and very attractive foliage. Color (young foliage): Upper surface: light green, Yellow-Green Group 146C, edged and more or less widely stained with reddish coloration. Under Surface: light green, Yellow-Green Group 146C, edged and more or less widely stained with reddish coloration. Color (adult foliage): Upper surface: dark green, Green Group 137A. Under surface: medium green, Green Group 138A.

Inflorescence:

*Number of flowers.*—Generally one per stem.

*Peduncle.*—Dark green and smooth. The length is approximately 11 to 12 cm. on average.

*Sepals.*—Upper surface: tomentose, greenish in coloration. Under surface: medium green and more or less tinted with reddish coloration. The outer sepals tend to have only slightly appendiculated edges. Sometimes a sepal is malformed and terminates in the form of a somewhat leaf-like appendix.

*Buds.*—Shape: conical. Length: approximately 3.5 cm. on average. Size: medium. Color upon opening: Upper surface: current red, Red Group 46A. Under surface: dark cardinal red, Red Group 53A.

*Flower.*—Shape: oval and very double. Diameter: approximately 9 to 10 cm. on average. Color: (when opening begins): Upper surface: strawberry red, Red Group 46B. Under surface: cardinal red, Red Group 53B. Color (when blooming): Upper surface: strawberry red, Red 46B. Under surface: cardinal red, Red Group 53B. Color (at end of opening): Upper surface: strawberry red, Red Group 46B. Under surface: cardinal red, Red Group 53B. Fragrance: none. Lasting quality: long lasting either on the plant or when cut and placed in a vase. Petal number: approximately 42 to 45 on average with approximately 2 to 3 petaloids, sometimes malformed and have a medium white vein. Texture: very consistent. Petal drop: excellent. Petal shape: commonly flat with corrugated and hem-like edges. Stamen number: approximately 160 to 170 on average. Anthers: light fuschia edged with ochre, and with end insertion. Filaments: free standing, greenish at the lower end and turning fuschia near the top, of irregular heights. Pistils: approximately 134 to 140 on average. Stigmas: straw colored, sometimes two are bonded together. Styles: greenish straw in coloration, tomentose at the base, and of irregular heights. Receptacle: light green in coloration, smooth, in longitudinal section it is in the shape of a pitcher.

Development:

*Vegetation.*—Very vigorous.

*Blooming.*—Average.

*Resistance to diseases.*—Very good.

*Aptitude to forcing.*—Average.

I claim:

1. A new and distinct variety of Hybrid Tea rose plant characterized by the following combination of characteristics:

(a) forms attractive long lasting double blossoms having very firm petals which are strawberry red on the upper surface and cardinal red on the under surface;

(b) exhibits an upright growth habit, (c) exhibits very vigorous vegetation, (d) is particularly suited for cut flower production in a greenhouse, and (e) exhibits very good disease resistance;

substantially as herein shown and described, and the parts thereof.

* * * * *

MEIDIAPLOU